United States Patent
Obrecht et al.

(10) Patent No.: US 9,556,231 B2
(45) Date of Patent: *Jan. 31, 2017

(54) BETA-HAIRPIN PEPTIDOMIMETICS AS CXC4 ANTAGONISTS

(71) Applicant: POLYPHOR AG, Allschwil (CH)

(72) Inventors: Daniel Obrecht, Bättwil (CH); Frank Otto Gombert, Basel (CH); Johann Zimmermann, Auggen (DE)

(73) Assignee: POLYPHOR AG, Allschwil (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/732,454

(22) Filed: Jun. 5, 2015

(65) Prior Publication Data

US 2015/0266924 A1    Sep. 24, 2015

Related U.S. Application Data

(63) Continuation of application No. 14/124,508, filed as application No. PCT/EP2012/060763 on Jun. 6, 2012, now Pat. No. 9,079,939.

(30) Foreign Application Priority Data

Jun. 7, 2011   (WO) .................. PCT/EP2011/059402

(51) Int. Cl.
  *A61K 38/00* (2006.01)
  *C07K 7/08* (2006.01)
  *C07K 7/64* (2006.01)
  *C07K 1/04* (2006.01)

(52) U.S. Cl.
  CPC .................. *C07K 7/08* (2013.01); *A61K 38/00* (2013.01); *C07K 1/047* (2013.01); *C07K 7/64* (2013.01)

(58) Field of Classification Search
  None
  See application file for complete search history.

(56) References Cited

FOREIGN PATENT DOCUMENTS

| WO | WO 2004/096840 A1 | 11/2004 |
|---|---|---|
| WO | WO 2010/060479 A1 | 6/2010 |

OTHER PUBLICATIONS

The Merck Manual: Human Immunodeficiency Virus (HIV) Infection: Human Immunodeficiency Virus (2014) pp. 1-25.*
HIV/AIDS Prevention Mayo Clinic 2016 pp. 1-3.*
International Search Report, issued in PCT/EP2012/060763, dated Jul. 6, 2012.

* cited by examiner

*Primary Examiner* — Thomas S Heard
(74) *Attorney, Agent, or Firm* — Birch, Stewart, Kolasch & Birch, LLP (57) ABSTRACT

β-Hairpin peptidomimetics of the general formula cyclo(-Tyr$^1$-His$^2$-Xaa$^3$-Cys$^4$-Ser$^5$-Ala$^6$-Xaa$^7$-Xaa$^8$-Arg$^9$-Tyr$^{10}$-Cys$^{11}$-Tyr$^{12}$-Xaa$^{13}$-Aaa$^{14}$-$^D$Pro$^{15}$-Pro$^{16}$-), disulfide bond between Cys$^4$ and Cys$^{11}$, and pharmaceutically acceptable salts thereof, with Xaa$^3$, Xaa$^7$, Xaa$^8$, Xaa$^{13}$ and Xaa$^{14}$ being amino acid residues of certain types which are defined in the description and the claims, have favorable pharmacological properties and can be used for preventing HIV infections in healthy individuals or for slowing and halting viral progression in infected patients; or where cancer is mediated or resulting from CXCR4 receptor activity; or where immunological diseases are mediated or resulting from CXCR4 receptor activity; or for treating immunosuppression; or during apheresis collections of peripheral blood stem cells and/or as agents to induce mobilization of stem cells to regulate tissue repair.

These peptidomimetics can be manufactured by a process which is based on a mixed solid- and solution phase synthetic strategy.

11 Claims, 1 Drawing Sheet

BETA-HAIRPIN PEPTIDOMIMETICS AS CXC4 ANTAGONISTS

This application is a Continuation of copending application Ser. No. 14/124,508, filed on Mar. 18, 2014, which was filed as PCT International Application No. PCT/EP2012/060763 on Jun. 6, 2012, which claims the benefit under 35 U.S.C. §119(a) to PCT International Application No. PCT/EP2011/059402, filed on Jun. 7, 2011, all of which are hereby expressly incorporated by reference into the present application.

The present invention provides β-hairpin peptidomimetics which are having CXCR4 antagonizing activity and are embraced by the general disclosure of, but not specifically disclosed in WO2004/096840 A1.

The β-hairpin peptidomimetics of the invention are cyclo(-Tyr$^1$-His$^2$-Xaa$^3$-Cys$^4$-Ser$^5$-Ala$^6$-Xaa$^7$-Xaa$^8$-Arg$^9$-Tyr$^{10}$-Cys$^{11}$-Tyr$^{12}$-Xaa$^{13}$-Xaa$^{14}$-$^D$Pro$^{15}$-Pro$^{16}$-), disulfide bond between Cys$^4$ and Cys$^{11}$, and pharmaceutically acceptable salts thereof, with Xaa$^3$ being Ala, Tyr or Tyr(Me) as described herein below, Xaa$^7$ being $^D$Tyr, $^D$Tyr(Me) as described herein below or $^D$Pro, Xaa$^8$ being Dab or Orn(iPr) as described herein below, Xaa$^{13}$ being Gln or Glu, and Xaa$^{14}$ being Lys(iPr), as described herein below.

In addition, the present invention provides an efficient synthetic process by which these compounds can, if desired, be made in parallel library-format. These β-hairpin peptidomimetics have favorable pharmacological properties and, in addition, show suitable plasma protein binding and appropriate clearance rates. Therefore they can be used as active ingredients in low amounts for all kind of drug formulations, in particular extended release drug formulations.

Many medically significant biological processes are mediated by signal transduction that involves chemokines and their receptors in general and stromal derived factor 1 (SDF-1/CXCL12) and its receptor CXCR4 in particular.

CXCR4 and its ligand SDF-1 are involved in trafficking of B-cells, hematopoietic stem cells (HSC) and hematopoietic progenitor cells (HPC). For instance, CXCR4 is expressed on CD34+ cells and has been implicated in the process of CD34+ cell migration and homing (S. M. Watt, S. P. Forde, *Vox sanguinis* 2008, 94, 18-32). It has also been shown that the CXCR4 receptor plays an important role in the release of stem and progenitor cells from the bone marrow to the peripheral blood (L. M. Pelus, S. Fukuda, *Leukemia* 2008, 22, 466-473). This activity of CXCR4 could be very important for efficient apheresis collections of peripheral blood stem cells. Autologous peripheral blood cells provide a rapid and sustained hematopoietic recovery following auto-transplantation after the administration of high-dose chemotherapy or radiotherapy in patients with haematological malignancies and solid tumors (W. C. Liles et al., *Blood* 2003, 102, 2728-2730).

Recently, it has been demonstrated that SDF-1 is locally up-regulated in animal models of injury including focal ischemic stroke, global cerebral ischemia, myocardial infarction and hind limb ischemia as well as being involved in recovery after peripheral ischemia or following injury to the liver, kidney or lung (A. E. Ting, R. W. Mays, M. R. Frey, W. Van't Hof, S. Mediccetty, R. Deans, *Critical Reviews in Oncology/Hematology* 2008, 65, 81-93 and literature cited herein; F. Lin, K. Cordes, L. Li, L. Hood, W. G. Couser, S. J. Shankland et al., *J. Am. Soc. Nephrol.* 2003, 14, 1188-1199; C. C. Dos Santos, *Intensive Care Med.* 2008, 34, 619-630). These results suggest that SDF-1 may be a chemoattractant for CXCR4-positive stem cells for tissue and organ repair/regeneration (M. Z. Ratajczak, M. Kucia, R. Reca, M. Majka, A. Janowska-Wieczorek, J. Ratajczak, *Leukemia* 2004, 18, 29-40). Therefore, modulating the SDF-1/CXCR4 axis by CXCR4 inhibitors should result in a significant therapeutic benefit by using released stem cells to regulate tissue repair.

More recently, it has been shown that disrupting the CXCR4/SDF-1 axis by CXCR4 inhibitors plays a crucial role in differential mobilization of progenitor cells like HPCs, endothelial (EPCs) and stromal progenitor cells (SPCs) from the bone marrow (S. C. Pitchford, R. C. Furze, C. P. Jones, A. M. Wegner, S. M. Rankin, *Cell Stem Cell* 2009, 4, 62). In addition, bone marrow-derived CXCR4$^+$ Very Small Embryonic-Like Stem Cells (VSELs) were mobilized in patients with acute myocardial infarction indicating a hypothetical reparatory mechanism (W. Wojakowski, M. Tendra, M. Kucia, E. Zuba-Surma, E. Paczkowska, J. Ciosek, M. Halasa, M. Kral, M. Kazmierski, P. Buszman, A. Ochala, J. Ratajczak, B. Machalinski, M. Z. Ratajczak, *J. Am. Coll. Cardiol.* 2009, 53, 1). These findings may be exploited to provide efficacious stem cell therapy for tissue regeneration.

Mesenchymal stem cells (MSC) are nonhematopoietic progenitor cells having the capability of differentiating into tissues such as bone and cartilage (D. J. Prockop, *Science* 1997, 276, 71). As a small proportion of MSCs strongly expresses functionally active CXCR4, modulation of the CXCR4/SDF-1 axis may mediate specific migration and homing of these cells (R. F. Wynn, C. A. Hart, C. Corradi-Perini, L. O'Neill, C. A. Evans, J. E. Wraith, L. J. Fairbaim, I. Bellantuono, *Blood* 2004, 104, 2643).

There is increasing evidence suggesting that chemokines in general and the SDF-1/CXCR4 interaction in particular play a pivotal role in angiogenesis. Chemokines induce angiogenesis directly by binding their cognate receptors on endothelial cells or indirectly by promoting inflammatory cell infiltrates, which deliver other angiogenic stimuli. A number of proinflammatory chemokines including interleukin 8 (IL-8), growth-regulated oncogene, stromal cell-derived factor 1 (SDF-1), monocyte chemotactic protein 1 (MCP-1), eotaxin 1, and 1-309 have been shown to act as direct inducers of angiogenesis (X. Chen, J. A. Beutler, T. G. McCloud, A. Loehfelm, L. Yang, H. F. Dong, O. Y. Chertov, R. Salcedo, J. J. Oppenheim, O. M. Howard. *Clin. Cancer Res.* 2003, 9(8), 3115-3123; R. Salcedo, J. J. Oppenheim, *Microcirculation* 2003, (3-4), 359-370).

Recently obtained results show that the CXCR4 receptor is involved in the chemotactic activity of cancer cells, such as breast cancer metastasis or in metastasis of ovarian cancer (A. Muller, B. Homey, H. Soto, N. Ge, D. Catron, M. E. Buchanan, T. Mc Clanahan, E. Murphey, W. Yuan, S. N. Wagner, J. L. Barrera, A. Mohar, E. Verastegui, A. Zlotnik, *Nature* 2001, 50, 410; J. M. Hall, K. S. Korach, *Molecular Endocrinology* 2003, 17, 792-803), Non-Hodgin's Lymphoma (F. Bertolini, C. Dell'Agnola, P. Manusco, C. Rabascio, A. Burlini, S. Monestiroli, A. Gobbi, G. Pruneri, G. Martinelli, *Cancer Research* 2002, 62, 3106-3112), or lung cancer (T. Kijima, G. Maulik, P. C. Ma, E. V. Tibaldi, R. E. Turner, B. Rollins, M. Sattler, B. E. Johnson, R. Salgia, *Cancer Research* 2002, 62, 6304-6311), melanoma, prostate cancer, kidney cancer, neuroblastomia, pancreatic cancer, multiple myeloma, chronic lymphocytic leukemia, hepatocellular carcinoma, colorectal carcinoma, endometrial cancer and germ cell tumor (H. Tamamura et al., *FEBS Letters* 2003, 550, 79-83, cited ref.; Z. Wang, Q. Ma, Q. Liu, H. Yu, L. Zhao, S. Shen, J. Yao, British *Journal of Cancer* 2008, 99, 1695; B. Sung, S. Jhurani, K. S. Ahn, Y. Mastuo, T. Yi, S. Guha, M. Liu, B. Aggarwal, *Cancer Res.* 2008, 68, 8938; H.

Liu, Z. Pan, A. Li, S. Fu, Y. Lei, H. Sun, M. Wu, W. Zhou, *Cellular and Molecular Immunology*, 2008, 5, 373; C. Rubie, O. Kollmar, V. O. Frick, M. Wagner, B. Brittner, S. Gräber, M. K. Schilling, *Scandinavian Journal of Immunology* 2008, 68, 635; S. Gelmini, M. Mangoni, F. Castiglioe, C. Beltrami, A. Pieralli, K. L. Andersson, M. Fambrini, G. I. Taddie, M. Serio, C. Orlando, *Clin. Exp. Metastasis* 2009, 26, 261; D. C. Gilbert, I. Chandler, A. McIntyre, N. C. Goddard, R. Gabe, R. A. Huddart, J. Shipley, *J. Pathol.* 2009, 217, 94). Blocking the chemotactic activity with a CXCR4 inhibitor should stop the migration of cancer cells and thus metastasis.

CXCR4 has also been implicated in the growth and proliferation of solid tumors and leukemia/lymphoma. It was shown that activation of the CXCR4 receptor was critical for the growth of both malignant neuronal and glial tumors. Moreover, systemic administration of the CXCR4 antagonist AMD3100 inhibits growth of intracranial glioblastoma and medulloblastoma xenografts by increasing apoptosis and decreasing the proliferation of tumor cells (J. B. Rubin, A. L Kung, R. S Klein, J. A. Chan, Y. Sun, K. Schmidt, M. W. Kieran, A. D. Luster, R. A. Segal, *Proc Natl Acad Sci USA*. 2003, 100(23), 13513-13518; S. Barbero, R. Bonavia, A. Bajetto, C. Porcile, P. Pirani, J. L. Ravetti, G. L. Zona, R. Spaziante, T. Florio, G. Schettini, *Cancer Res.* 2003, 63(8), 1969-1974; T. Kijima, G. Maulik, P. C. Ma, E. V. Tibaldi, R. E. Turner, B. Rollins, M. Sattler, B. E. Johnson, R. Salgia. *Cancer Res.* 2002, 62(21), 6304-6311). CXCR4 inhibitors also showed promising in vitro and in vivo efficacies in breast cancer, small cell lung cancer, pancreatic cancer, gastric cancer, colorectal cancer, malignant melanoma, ovarian cancer, rhabdomyo-sarcoma, prostate cancer as well as chronic lymphocytic leukemia, acute myelogenous leukemia, acute lymphoblastic leukemia, multiple myeloma and Non-Hodgkin's lymphoma (J. A. Burger, A. Peled, *Leukemia* 2009, 23, 43-52 and literature cited herein).

It is well established that chemokines are involved in a number of inflammatory pathologies and some of them show a pivotal role in the modulation of osteoclast development. Immunostaining for SDF-1 (CXCL12) on synovial and bone tissue biopsies from both rheumatoid arthritis (RA) and osteoarthritis (OA) samples have revealed strong increases in the expression levels of chemokines under inflammatory conditions (F. Grassi, S. Cristino, S. Toneguzzi, A. Piacentini, A. Facchini, G. Lisignoli, *J. Cell Physiol.* 2004; 199(2), 244-251). It seems likely that the CXCR4 receptor plays an important role in inflammatory diseases such as rheumatoid arthritis, asthma, multiple sclerosis, Alzheimer's disease, Parkinson's disease, atherosclerosis, or eye diseases such as diabetic retinopathy and age related macular degeneration (K. R. Shadidi et al., *Scandinavian Journal of Immunology* 2003, 57, 192-198; J. A. Gonzalo, *J. Immunol.* 2000, 165, 499-508; S. Hatse et al., *FEBS Letters* 2002, 527, 255-262 and cited references, A. T. Weeraratna, A. Kalehua, I. DeLeon, D. Bertak, G. Maher, M. S. Wade, A. Lustig, K. G. Becker, W. Wood, D. G. Walker, T. G. Beach, D. D. Taub, *Exp. Cell Res.* 2007, 313, 450; M. Shimoji, F. Pagan, E. B. Healton, I. Mocchetti, *Neurotox. Res.* 2009, 16, 318; A. Zernecke, E. Shagdarsuren, C. Weber, *Arteriosder. Thromb. Vasc. Biol.* 2008, 28, 1897; R. Lima e Silva, J. Shen, S. F. Hackett, S. Kachi, H. Akiyama et al., *FASEB* 2007, 21, 3219). The mediation of recruitment of immune cells to sites of inflammation should be stopped by a CXCR4 inhibitor.

To date the available therapies for the treatment of HIV infections have been leading to a remarkable improvement in symptoms and recovery from disease in infected people. Although the highly active anti-retroviral therapy (HAART) which involves a combination of reverse transcriptase/protease-inhibitor has dramatically improved the clinical treatment of individuals with AIDS or HIV infection, there have still remained several serious problems including multi drug resistance, significant adverse effects and high costs. Particularly desired are anti-HIV agents that block the HIV infection at an early stage of the infection, such as the viral entry. It has recently been recognized that for efficient entry into target cells, human immunodeficiency viruses require the chemokine receptors CCR5 and CXCR4 as well as the primary receptor CD4 (N. Levy, *Engl. J. Med.* 1996, 335, 1528-1530). Accordingly, an agent which could block the CXCR4 chemokine receptors should prevent infections in healthy individuals and slow or halt viral progression in infected patients (J. Cohen, *Science* 1997, 275, 1261-1264).

Among the different types of CXCR4 inhibitors (M. Schwarz, T. N. C. Wells, A. E. I. Proudfoot, *Receptors and Channels* 2001, 7, 417-428; Y. Lavrovsky, Y. A. Ivanenkov, K. V. Balakin, D. A. Medvedewa, P. V. Ivachtchenko, *Mini Rev. Med. Chem.* 2008, 11, 1075-1087), one emerging class is based on naturally occurring cationic peptide analogues derived from Polyphemusin II which have an antiparallel β-sheet structure, and a β-hairpin that is maintained by two disulfide bridges (H. Nakashima, M. Masuda, T. Murakami, Y. Koyanagi, A. Matsumoto, N. Fujii, N. Yamamoto, *Antimicrobial Agents and Chemoth.* 1992, 36, 1249-1255; H. Tamamura, M. Kuroda, M. Masuda, A. Otaka, S. Funakoshi, H. Nakashima, N. Yamamoto, M. Waki, A. Matsumotu, J. M. Lancelin, D. Kohda, S. Tate, F. Inagaki, N. Fujii, *Biochim. Biophys. Acta* 1993, 209, 1163; WO 95/10534 A1).

Synthesis of structural analogs and structural studies by nuclear magnetic resonance (NMR) spectroscopy have shown that the cationic peptides adopt well defined β-hairpin conformations, due to the constraining effect of one or two disulfide bridges (H. Tamamura, M. Sugioka, Y. Odagaki, A. Omagari, Y. Kahn, S. Oishi, H. Nakashima, N. Yamamoto, S. C. Peiper, N. Hamanaka, A. Otaka, N. Fujii, *Bioorg. Med. Chem. Lett.* 2001, 359-362). These results show that the β-hairpin structure plays an important role in CXCR4 antagonizing activity.

Additional structural studies have indicated that the antagonizing activity can also be influenced by modulating amphiphilic structure and the pharmacophore (H. Tamamura, A. Omagari, K. Hiramatsu, K. Gotoh, T. Kanamoto, Y. Xu, E. Kodama, M. Matsuoka, T. Hattori, N. Yamamoto, N. Nakashima, A. Otaka, N. Fujii, *Bioorg. Med. Chem. Lett.* 2001, 11, 1897-1902; H. Tamamura, A. Omagari, K. Hiramatsu, S. Oishi, H. Habashita, T. Kanamoto, K. Gotoh, N. Yamamoto, H. Nakashima, A. Otaka N. Fujii, *Bioorg. Med. Chem.* 2002, 10, 1417-1426; H. Tamamura, K. Hiramatsu, K. Miyamoto, A. Omagari, S. Oishi, H. Nakashima, N. Yamamoto, Y. Kuroda, T. Nakagawa, A. Otaki, N. Fujii, *Bioorg. Med. Chem. Letters* 2002, 12, 923-928).

The compounds cyclo(-Tyr$^1$-His$^2$-Xaa$^3$-Cys$^4$-Ser$^5$-Ala$^6$-Xaa$^7$-Xaa$^8$-Arg$^9$-Tyr$^{10}$-Cys$^{11}$-Tyr$^{12}$-Xaa$^{13}$-Xaa$^{14}$-$^D$Pro$^{15}$-Pro$^{16}$-), disulfide bond between Cys$^4$ and Cys$^{11}$, of the invention are cyclic β-hairpin peptidomimetics exhibiting high CXCR4 antagonizing activity, being useful for efficient apheresis collections of mobilized peripheral blood stem cells and/or using these mobilized cells to regulate tissue repair, and/or having anti-cancer activity, anti-inflammatory activity and/or anti-HIV activity.

The cyclic β-hairpin conformation is induced by the D-amino acid residue Xaa⁷ and the D-amino acid residue $^D$Pro¹⁵. Further stabilization of the hairpin conformation is achieved by the amino acid residues Cys at positions 4 and 11, which, taken together, form a disulfide bridge.

Surprisingly we have found that the introduction of the basic amino acid residue Lys(iPr) at position 14, supported by the optional introduction of Orn(iPr) at position 8 of cyclo(-Tyr¹-His²-Xaa³-Cys⁴-Ser⁵-Ala⁶-Xaa⁷-Xaa⁸-Arg⁹-Tyr¹⁰-Cys¹¹-Tyr¹²-Xaa¹³-Xaa¹⁴-$^D$Pro¹⁵-Pro¹⁶-), disulfide bond between Cys⁴ and Cys¹¹, result in β-hairpin peptidomimetics which have favorable pharmacological properties. These properties, combined with suitable plasma protein binding and appropriate clearance rates form a pharmacological profile which allows these compounds to be used as active ingredients in low amounts for all kind of drug formulations, in particular extended release drug formulations.

The β-hairpin peptidomimetics of the present invention are compounds of the general formula cyclo(-Tyr¹-His²-Xaa³-Cys⁴-Ser⁵-Ala⁶-Xaa⁷-Xaa⁸-Arg⁹-Tyr¹⁰-Cys¹¹-Tyr¹²-Xaa¹³-Xaa¹⁴-$^D$Pro¹⁵-Pro¹⁶-)  (I), disulfide bond between Cys⁴ and Cys¹¹, and pharmaceutically acceptable salts thereof,
wherein
Xaa³ is Ala, Tyr or Tyr(Me), the latter being (2S)-2-amino-(4-methoxyphenyl)-3-propionic acid,
Xaa⁷ is $^D$Tyr, $^D$Tyr(Me), i.e. (2R)-2-amino-(4-methoxyphenyl)-3-propionic acid, or $^D$Pro,
Xaa⁸ is Dab, i.e. (2S)-2,4-diaminobutyric acid, or Orn(iPr), i.e. (2S)—N^ω-isopropyl-2,5-diaminopentanoic acid,
Xaa¹³ is Gln or Glu,
Xaa¹⁴ is Lys(iPr), i.e. (2S)—N^ω-isopropyl-2,6-diaminohexanoic acid.

In a particular embodiment of the present invention the β-hairpin peptidomimetics are compounds of the general formula I, in which Xaa¹³ is Gln, and pharmaceutically acceptable salts thereof.

In another particular embodiment of the present invention the β-hairpin peptidomimetics are compounds of the general formula I, in which Xaa³ is Tyr; or Tyr(Me), Xaa⁷ is $^D$Pro, Xaa⁸ is Orn(iPr) and Xaa¹³ is Gln, and pharmaceutically acceptable salts thereof.

In a preferred embodiment of the present invention the compound is cyclo(-Tyr¹-His²-Ala³-Cys⁴-Ser⁵-Ala⁶-$^D$Tyr⁷-Dab⁸-Arg⁹-Tyr¹⁰-Cys¹¹-Tyr¹²-Gln¹³-Lys(iPr)¹⁴-$^D$Pro¹⁵-Pro¹⁶-), disulfide bond between Cys⁴ and Cys¹¹, and pharmaceutically acceptable salts thereof.

In another preferred embodiment of the present invention the compound is cyclo(-Tyr¹-His²-Tyr³-Cys⁴-Ser⁵-Ala⁶-$^D$Pro⁷-Orn(iPr)⁸-Arg⁹-Tyr¹⁰-Cys¹¹-Tyr¹²-Gln¹³-Lys(iPr)¹⁴-$^D$Pro¹⁵-Pro¹⁶-) disulfide bond between Cys⁴ and Cys¹¹, and pharmaceutically acceptable salts thereof.

In another preferred embodiment of the present invention the compound is cyclo(-Tyr¹-His²-Tyr(Me)³-Cys⁴-Ser⁵-Ala⁶-$^D$Pro⁷-Orn(iPr)⁸-Arg⁹-Tyr¹⁰-Cys¹¹-Tyr¹²-Gln¹³-Lys(iPr)¹⁴-$^D$Pro¹⁵-Pro¹⁶-), disulfide bond between Cys⁴ and Cys¹¹, and pharmaceutically acceptable salts thereof.

In another preferred embodiment of the present invention the compound is cyclo(-Tyr¹-His²-Ala³-Cys⁴-Ser⁵-Ala⁶-$^D$Tyr(Me)⁷-Orn(iPr)⁸-Arg⁹-Tyr¹⁰-Cys¹¹-Tyr¹²-Gln¹³-Lys(iPr)¹⁴-$^D$Pro¹⁵-Pro¹⁶-), disulfide bond between Cys⁴ and Cys¹¹, and pharmaceutically acceptable salts thereof.

In another preferred embodiment of the present invention the compound is cyclo(-Tyr¹-His²-Tyr³-Cys⁴-Ser⁵-Ala⁶-$^D$Tyr⁷-Orn(iPr)⁸-Arg⁹-Tyr¹⁰-Cys¹¹-Tyr¹²-Gln¹³-Lys(iPr)¹⁴-$^D$Pro¹⁵-Pro¹⁶-), disulfide bond between Cys⁴ and Cys¹¹, and pharmaceutically acceptable salts thereof.

In still another preferred embodiment of the present invention the compound is cyclo(-Tyr¹-His²-Tyr(Me)³-Cys⁴-Ser⁵-Ala⁶-$^D$Tyr(Me)⁷-Orn(iPr)⁸-Arg⁹-Tyr¹⁰-Cys¹¹-Tyr¹²-Gln¹³-Lys(iPr)¹⁴-$^D$Pro¹⁵-Pro¹⁶-), disulfide bond between Cys⁴ and Cys¹¹, and pharmaceutically acceptable salts thereof.

In accordance with the present invention these β-hairpin peptidomimetics can be prepared by a process which comprises (a) coupling an appropriately functionalized solid support with an appropriately N-protected derivative of Pro which is in the desired end-product in position 16;
(b) removing the N-protecting group from the product thus obtained;
(c) coupling the product thus obtained with an appropriately N-protected derivative of $^D$Pro which is in the desired end-product in position 15;
(d) removing the N-protecting group from the product obtained in step (c);
(e) effecting steps substantially corresponding to steps (c) and (d) using appropriately N-protected derivatives of amino acids which in the desired end-product are in positions 14 to 1, any functional group(s) which may be present in said N-protected amino acid derivatives being likewise appropriately protected;
(f) if desired, forming a disulfide bridge between the side-chains of the Cys residues at position 4 and position 11; or alternatively, forming the aforesaid linkage subsequent to step (i), as described herein below;
(g) detaching the product thus obtained from the solid support;
(h) cyclizing the product cleaved from the solid support;
(i) removing any protecting groups present on functional groups of any members of the chain of amino acid residue; and
(j) if desired, attaching one or several isopropyl groups
(k) if required, removing any protecting groups present on functional groups of any members of the chain of amino acid and
(l) if desired, converting the product thus obtained into a pharmaceutically acceptable salt or converting a pharmaceutically acceptable, or unacceptable, salt thus obtained into the corresponding free compound or into a different, pharmaceutically acceptable, salt.

The β-hairpin peptidomimetics of this invention can be produced, for example, by following a procedure comprising the synthesis of the linear peptide on resin whereas the isopropyl group-bearing amino acid residue(s) Orn(iPr) or Lys(iPr) will be incorporated as amino acid building block(s) being commercially available or synthesized beforehand; or a procedure comprising the synthesis of a linear peptide on resin by applying an orthogonal protecting group strategy whereas, for example, all amino group-bearing side chains of amino acid residues which are not considered to be modified shall be protected by ivDde or the like so that amino group-bearing side chains of amino acid residues protected by acid labile protecting groups suitable to the Fmoc-based solid phase peptide synthesis strategy can be derivatized by coupling isopropyl groups in solution at a very late stage of the synthesis cascade; or following a procedure comprising a suitable combination of the procedures described before.

The proper choice of the functionalized solid-support (i.e. solid support plus linker molecule) and the site of cyclization play key roles in the synthesis process of the β-hairpin peptidomimetics of the invention.

The functionalized solid support is conveniently derived from polystyrene crosslinked with, preferably 1-5%, divinylbenzene; polystyrene coated with polyethyleneglycol spacers (Tentagel®); and polyacrylamide resins (D. Obrecht, J.-M. Villalgordo, "Solid-Supported Combinatorial and Parallel Synthesis of Small-Molecular-Weight Compound Libraries", *Tetrahedron Organic Chemistry Series*, Vol. 17, Pergamon, Elsevier Science, 1998).

The solid support is functionalized by means of a linker, i.e. a bifunctional spacer molecule which contains on one end an anchoring group for attachment to the solid support and on the other end a selectively cleavable functional group used for the subsequent chemical transformations and cleavage procedures. For the purposes of the present invention two types of linkers are used:

Type 1 linkers are designed to release the amide group under acidic conditions (H. Rink, *Tetrahedron Lett.* 1987, 28, 3783-3790). Linkers of this kind form amides of the carboxyl group of the amino acids; examples of resins functionalized by such linker structures include 4-[(((2,4-dimethoxy-phenyl)Fmoc-aminomethyl) phenoxyacetamido) aminomethyl] PS resin, 4-[(((2,4-dimethoxyphenyl) Fmoc-aminomethyl)phenoxy-acetamido)aminomethyl]-4-methylbenzhydrylamine PS resin (Rink amide MBHA PS Resin), and 4-[(((2,4-dimethoxy-phenyl) Fmoc-aminomethyl)phenoxyacetamido)aminomethyl]benzhydrylamine PS-resin (Rink amide BHA PS resin). Preferably, the support is derived from polystyrene crosslinked with, most preferably 1-5%, divinylbenzene and functionalized by means of the 4-(((2,4-dimethoxyphenyl) Fmoc-aminomethyl)phenoxyacetamido) linker.

Type 2 linkers are designed to eventually release the carboxyl group under acidic conditions. Linkers of this kind form acid-labile esters with the carboxyl group of the amino acids, usually acid-labile benzyl, benzhydryl and trityl esters; examples of such linker structures include 2-methoxy-4-hydroxymethylphenoxy (Sasrin® linker), 4-(2,4-dimethoxyphenyl-hydroxymethyl)-phenoxy (Rink linker), 4-(4-hydroxymethyl-3-methoxyphenoxy)butyric acid (HMPB linker), trityl and 2-chlorotrityl. Preferably, the support is derived from polystyrene crosslinked with, most preferably 1-5%, divinyl-benzene and functionalized by means of the 2-chlorotrityl linker.

When carried out as parallel array syntheses the processes of the invention can be advantageously carried out as described herein below but it will be immediately apparent to those skilled in the art how these procedures will have to be modified in case it is desired to synthesize one single compound of the invention.

A number of reaction vessels equal to the total number of compounds to be synthesized by the parallel method are loaded with 25 to 1000 mg, preferably 60 mg, of the appropriate functionalized solid support, preferably 1 to 3% cross-linked polystyrene or Tentagel resin.

The solvent to be used must be capable of swelling the resin and includes, but is not limited to, dichloromethane (DCM), dimethylformamide (DMF), N-methylpyrrolidone (NMP), dioxane, toluene, tetrahydrofuran (THF), ethanol (EtOH), trifluoroethanol (TFE), isopropylalcohol and the like. Solvent mixtures containing as at least one component a polar solvent (e.g. 20% TFE/DCM, 35% THF/NMP) are beneficial for ensuring high reactivity and solvation of the resin-bound peptide chains (G. B. Fields, C. G. Fields, *J. Am. Chem. Soc.* 1991, 113, 4202-4207).

With the development of various linkers that release the C-terminal carboxylic acid group under mild acidic conditions, not affecting acid-labile groups protecting functional groups in the side chain(s), considerable progresses have been made in the synthesis of protected peptide fragments. The 2-methoxy-4-hydroxybenzylalcohol-derived linker (Sasrin® linker, Mergler et al., *Tetrahedron Lett.* 1988, 29 4005-4008) is cleavable with diluted trifluoroacetic acid (0.5-1% TFA in DCM) and is stable to Fmoc deprotection conditions during the peptide synthesis, Boc/tBu-based additional protecting groups being compatible with this protection scheme. Other linkers which are suitable for the process of the invention include the super acid labile 4-(2,4-dimethoxyphenyl-hydroxymethyl)-phenoxy linker (Rink linker, H. Rink, *Tetrahedron Lett.* 1987, 28, 3787-3790), where the removal of the peptide requires 10% acetic acid in DCM or 0.2% trifluoroacetic acid in DCM; the 4-(4-hydroxymethyl-3-methoxyphenoxy)butyric acid-derived linker (HMPB-linker, Flörsheimer & Riniker, *Peptides* 1991, 1990 131) which is also cleaved with 1% TFA/DCM in order to yield a peptide fragment containing all acid labile side-chain protective groups; and, in addition, the 2-chlorotritylchloride linker (Barlos et al., *Tetrahedron Lett.* 1989, 30, 3943-3946), which allows the peptide detachment using a mixture of glacial acetic acid/trifluoroethanol/DCM (1:2:7) for 30 min.

Suitable protecting groups for amino acids and, respectively, for their residues are, for example, for the amino group (as is present e.g. also in the side-chain of lysine or ornithine)
Cbz benzyloxycarbonyl
Boc tert-butyloxycarbonyl
Fmoc 9-fluorenylmethoxycarbonyl
Alloc allyloxycarbonyl
Teoc trimethylsilylethoxycarbonyl
Tcc trichloroethoxycarbonyl
Nps o-nitrophenylsulfonyl;
Trt triphenymethyl or trityl
ivDde (4,4-dimethyl-2,6-dioxocyclohex-1-ylidene)-3-methylbutyl
for the carboxyl group (as is present e.g. also in the side-chain of glutamic acid) by conversion into esters with the alcohol components
tBu tert-butyl
Bn benzyl
Me methyl
Ph phenyl
Pac phenacyl
allyl
Tse trimethylsilylethyl
Tce trichloroethyl;
ivDde (4,4-dimethyl-2,6-dioxocyclohex-1-ylidene)-3-methylbutyl
for the guanidino group (as is present e.g. in the side-chain of arginine)
Pmc 2,2,5,7,8-pentamethylchroman-6-sulfonyl
Ts tosyl (i. e. p-toluenesulfonyl)
Cbz benzyloxycarbonyl
Pbf pentamethyldihydrobenzofuran-5-sulfonyl
for the hydroxy group (as is present e.g. in the side-chain of serine)
tBu tert-butyl
Bn benzyl Trt trityl
Alloc allyloxycarbonyl
and for the mercapto group (as is present e.g. in the side-chain of cysteine)
Acm acetamidomethyl
tBu tert-butyl
Bn benzyl
Trt trityl
Mtr 4-methoxytrityl.

The 9-fluorenylmethoxycarbonyl (Fmoc)-protected amino acid derivatives are preferably used as the building blocks for the construction of the β-hairpin loop mimetics of the invention. For the deprotection, i. e. cleaving off of the Fmoc group, 20% piperidine in DMF or 2% DBU/2% piperidine in DMF can be used.

The linkage of isopropyl groups to amino group-bearing side chains of 9-fluorenylmethoxycarbonyl (Fmoc)-protected amino acid derivatives to form isopropylated amino group-bearing side chains of (Fmoc)-protected amino acid derivatives is known in the art. The procedure for introducing an isopropyl group can be accomplished e.g. by reductive alkylation e.g. treatment of the amino group of the amino group-bearing side chain of an amino acid building block like e.g. Orn with acetone in the presence of a suitable reducing agent like e.g. sodium triacetoxyborohydride. Protecting groups like e.g Boc suitable for isopropylated amino group-bearing side chains of (Fmoc)-protected amino acid derivatives can be introduced by subsequent reaction with di-tert-butyl dicarbonate in the presence of a base such as sodium bicarbonate.

The quantity of the reactant, i. e. of the amino acid derivative, is usually 1 to 20 equivalents based on the milliequivalents per gram (meq/g) loading of the functionalized solid support (typically 0.1 to 2.85 meq/g for polystyrene resins) originally weighed into the reaction tube. Additional equivalents of reactants can be used, if required, to drive the reaction to completion in a reasonable time. The preferred workstations (without, however, being limited thereto) are Labsource's Combi-chem station, Protein Technologies' Symphony and MultiSyn Tech's-Syro synthesizer, the latter additionally equipped with a transfer unit and a reservoir box during the process of detachment of the fully protected linear peptide from the solid support. All synthesizers are able to provide a controlled environment, for example, reactions can be accomplished at temperatures different from room temperature as well as under inert gas atmosphere, if desired.

Amide bond formation requires the activation of the α-carboxyl group for the acylation step. When this activation is being carried out by means of the commonly used carbodiimides such as dicyclohexylcarbodiimide (DCC, Sheehan & Hess, *J. Am. Chem. Soc.* 1955, 77, 1067-1068) or diisopropylcarbodiimide (DIC, Sarantakis et al *Biochem. Biophys. Res. Commun.* 1976, 73, 336-342), the resulting dicyclohexylurea and, respectively, diisopropylurea is insoluble and, respectively, soluble in the solvents generally used. In a variation of the carbodiimide method 1-hydroxybenzotriazole (HOBt, König & Geiger, *Chem. Ber.* 1970, 103, 788-798) is included as an additive to the coupling mixture. HOBt prevents dehydration, suppresses racemization of the activated amino acids and acts as a catalyst to improve the sluggish coupling reactions. Certain phosphonium reagents have been used as direct coupling reagents, such as benzotriazol-1-yl-oxy-tris-(dimethyl-amino)-phosphonium hexafluorophosphate (BOP, Castro et al., *Tetrahedron Lett.* 1975, 14, 1219-1222; *Synthesis* 1976, 751-752), or benzotriazol-1-yl-oxy-tris-pyrrolidino-phosphonium hexaflurophoshate (Py-BOP, Coste et al., *Tetrahedron Lett.* 1990, 31, 205-208), or 2-(1H-benzotriazol-1-yl-)1,1,3,3-tetramethyluronium tetrafluoroborate (TBTU), or hexafluorophosphate (HBTU, Knorr et al., *Tetrahedron Lett.* 1989, 30, 1927-1930); these phosphonium reagents are also suitable for in situ formation of HOBt esters with the protected amino acid derivatives. More recently diphenoxyphosphoryl azide (DPPA) or O-(7-aza-benzotriazol-1-yl)-N,N,N',N'-tetramethyluronium tetrafluoroborate (TATU) or O-(7-aza-benzotriazol-1-yl)-N,N,N',N'-tetramethyluronium hexafluorophosphate (HATU)/7-aza-1-hydroxy benzo-triazole (HOAt, Carpino et al., *Tetrahedron Lett.* 1994, 35, 2279-2281) or -(6-Chloro-1H-benzotriazol-1-yl-)-N,N,N',N'-1,1,3,3-tetramethyl-uronium tetrafluoroborate (TCTU), or hexafluorophosphate (HCTU, Marder, Shivo and Albericio: HCTU and TCTU: New Coupling Reagents: Development and Industrial Applications, Poster Presentation, Gordon Conference February 2002) have also been used as coupling reagents as well as 1,1,3,3-bis(tetramethylene)chlorouronium hexafluoro-phosphate (PyClU, especially for coupling N-methylated amino acids, J. Coste, E. Frérot, P. Jouin, B. Castro, *Tetrahedron Lett.* 1991, 32, 1967) or pentafluorophenyl diphenyl-phosphinate (S. Chen, J. Xu, *Tetrahedron Lett.* 1991, 32, 6711).

Due to the fact that near-quantitative coupling reactions are essential, it is desirable to have experimental evidence for completion of the reactions. The ninhydrin test (Kaiser et al., *Anal. Biochemistry* 1970, 34, 595), where a positive colorimetric response to an aliquot of resin-bound peptide indicates qualitatively the presence of the primary amine, can easily and quickly be performed after each coupling step. Fmoc chemistry allows the spectrophotometric detection of the Fmoc chromophore when it is released with the base (Meienhofer et al., *Int. J. Peptide Protein Res.* 1979, 13, 35-42).

The resin-bound intermediate within each reaction vessel is washed free of excess of retained reagents, of solvents, and of by-products by repetitive exposure to pure solvent(s) by one of the two following methods:

1) The reaction vessels are filled with solvent (preferably 5 mL), agitated for 5 to 300 minutes, preferably 15 minutes, and drained to expel the solvent;
2) The reaction vessels are filled with solvent (preferably 5 mL) and drained into a receiving vessel such as a test tube or vial.

Both of the above washing procedures are repeated up to about 50 times (preferably about 10 times), monitoring the efficiency of reagent, solvent, and by-product removal by methods such as TLC, GC, or inspection of the washings.

The above described procedure of reacting the resin-bound compound with reagents within the reaction tubes followed by removal of excess reagents, by-products, and solvents is repeated with each successive transformation until the final resin-bound fully protected linear peptide has been obtained.

Before this fully protected linear peptide is detached from the solid support, a disulfide bridge between $Cys^4$ and $Cys^{11}$ can be formed.

For the formation of a disulfide bridge preferably a solution of 10 equivalents of iodine solution is applied in DMF or in a mixture of $CH_2Cl_2$/MeOH for 1.5 h which is repeated for another 3 h with a fresh iodine solution after filtering of the iodine solution, or in a mixture of DMSO and acetic acid solution, buffered with 5% $NaHCO_3$ to pH 5-6 for 4 h, or in water after adjusting to pH 8 with ammonium hydroxide solution by stirring for 24 h, or in a solution of NMP and tri-n-butylphosphine (preferably 50 eq.).

Alternatively, the formation of the disulfide bridge between $Cys^4$ and $Cys^{11}$ can be carried out subsequent to the work-up method 2), as described herein below, by stirring the crude fully deprotected and cyclized peptide for 24 h in water containing DMSO up to 15% by volume, buffered with 5% $NaHCO_3$ to pH 5-6, or buffered with ammonium acetate to pH 7-8, or adjusted with ammonium hydroxide to pH 8. Following evaporation to dryness cyclo(-$Tyr^1$-$His^2$-$Xaa^3$-$Cys^4$-$Ser^5$-$Ala^6$-$Xaa^7$-$Xaa^8$-$Arg^9$-$Tyr^{10}$-$Cys^{11}$-$Tyr^{12}$-$Xaa^{13}$-$Xaa^{14}$-$^DPro^{15}$-$Pro^{16}$-), disulfide bond between $Cys^4$ and $Cys^{11}$ is obtained as end-product.

Detachment of the fully protected linear peptide from the solid support is achieved by exposing the loaded resin with a solution of the reagent used for cleavage (preferably 3 to 5 mL). Temperature control, agitation, and reaction monitoring are implemented as described above. Via a transfer-unit the reaction vessels are connected with a reservoir box containing reservoir tubes to efficiently collect the cleaved product solutions. The resins remaining in the reaction vessels are then washed 2 to 5 times as above with 3 to 5 mL of an appropriate solvent to extract (wash out) as much of the detached products as possible. The product solutions thus obtained are combined, taking care to avoid cross-mixing. The individual solutions/extracts are then manipulated as needed to isolate the final compounds. Typical manipulations include, but are not limited to, evaporation, concentration, liquid/liquid extraction, acidification, basification, neutralization or additional reactions in solution.

The solutions containing fully protected linear peptide derivatives which have been cleaved off from the solid support and neutralized with a base, are evaporated. Cyclization is then effected in solution using solvents such as DCM, DMF, dioxane, THF and the like. Various coupling reagents which were mentioned earlier can be used for the cyclization. The duration of the cyclization is about 6-48 h, preferably about 16 h. The progress of the reaction is followed, e. g. by RP-HPLC (Reverse Phase High Performance Liquid Chromatography). Then the solvent is removed by evaporation, the fully protected cyclic peptide derivative is dissolved in a solvent which is not miscible with water, such as DCM, and the solution is extracted with water or a mixture of water-miscible solvents, in order to remove any excess of the coupling reagent.

Finally, the fully protected peptide derivative is treated with 95% TFA, 2.5% $H_2O$, 2.5% TIS or another combination of scavengers for effecting the cleavage of protecting groups. The cleavage reaction time is commonly 30 minutes to 12 h, preferably about 2.5 h.

Alternatively, the detachment and complete deprotection of the fully protected peptide from the solid support can be achieved manually in glass vessels.

After full deprotection, for example, the following methods can be used for further work-up:
1) The volatiles are evaporated to dryness and the crude peptide is dissolved in 20% AcOH in water and extracted with isopropyl ether or other solvents which are suitable therefor. The aqueous layer is collected and evaporated to dryness, and the fully deprotected peptide, cyclo(-$Tyr^1$-$His^2$-$Xaa^3$-$Cys^4$-$Ser^5$-$Ala^6$-$Xaa^7$-$Xaa^8$-$Arg^9$-$Tyr^{10}$-$Cys^{11}$-$Tyr^{12}$-$Xaa^{13}$-$Xaa^{14}$-$^DPro^{15}$-$Pro^{16}$-), disulfide bond between $Cys^4$ and $Cys^{11}$, is obtained as final product;
2) The deprotection mixture is concentrated under vacuum. Following precipitation of the fully deprotected peptide in diethylether at preferably 0° C. the solid is washed up to about 10 times, preferably 3 times, dried, and the fully deprotected peptide, cyclo(-$Tyr^1$-$His^2$-$Xaa^3$-$Cys^4$-$Ser^5$-$Ala^6$-$Xaa^7$-$Xaa^8$-$Arg^9$-$Tyr^{10}$-$Cys^{11}$-$Tyr^{12}$-$Xaa^{13}$-$Xaa^{14}$-$^DPro^{15}$-$Pro^{16}$-), disulfide bond between $Cys^4$ and $Cys^{11}$, is obtained as final product, if a disulfide bond between $Cys^4$ and $Cys^{11}$ has been formed on solid support as described herein above.

If the above mentioned orthogonal protecting group strategy for introducing one or more isopropyl groups in solution has been followed, then all amino groups of side chains of amino acid residues are still protected by non-acid labile protecting groups whereas amino groups of amino acid residues formerly protected by acid labile protecting groups have been liberated at this stage of the synthesis cascade. Thus, it is possible, if desired, to couple an isopropyl group. Preferably, ivDde or the like are acid stable protecting groups for amino group bearing side chains which are kept unmodified during the coupling of isopropyl groups to liberated amino groups. This coupling can be accomplished by applying e.g. a reductive alkylation using acetone in the presence of a suitable reducing agent like e.g. sodium cyano borohydride. Thus, for example, the peptide is dissolved in MeOH (4.4 mM) containing acetic acid (0.2 M). After adding an excess of acetone (780 eq) the reaction mixture is completed with a solution of sodium cyano borohydride in MeOH (0.6 M; 1.3 eq per isopropyl group desired to be introduced) and vigorously shaken at room temperature. Following completion of the conversion monitored by LC-MS, water is added and the solvents are evaporated. The residual solid containing the peptide is dissolved in DMF (0.01 M) and a solution of 5% hydrazine in DMF is used to finally remove the ivDde-protecting groups.

As mentioned earlier, it is thereafter possible, if desired, to convert the fully deprotected cyclic product thus obtained into a pharmaceutically acceptable salt or to convert a pharmaceutically acceptable, or unacceptable, salt thus obtained into the corresponding free compound or into a different, pharmaceutically acceptable, salt. Any of these operations can be carried out by methods well known in the art.

The β-hairpin peptidomimetics of the invention can be used in a wide range of applications in order to prevent HIV infections in healthy individuals and slow or halt viral progression in infected patients, or where cancer is mediated or resulting from the CXCR4 receptor activity, or where immunological diseases are mediated or resulting from CXCR4 receptor activity; or these β-hairpin peptidomimetics can be used to treat immunosuppression, or they can be used during apheresis collections of peripheral blood stem cells and/or as agents to induce mobilization of stem cells to regulate tissue repair.

The β-hairpin peptidomimetics of the invention may be administered per se or may be applied as an appropriate formulation together with carriers, diluents or excipients well known in the art.

When used to treat or prevent HIV infections or cancer such as breast cancer, brain cancer, prostate cancer, heptatocellular carcinoma, colorectal cancer, lung cancer, kidney cancer, neuroblastoma, ovarian cancer, endometrial cancer, germ cell tumor, eye cancer, multiple myeloma, pancreatic cancer, gastric cancer, rhabdomyo-sarcoma, melanoma, chronic lyphomphocytic leukemia, acute myelogenous leukemia, acute lymphoblastic leukemia, multiple myeloma and Non-Hodgkin's lymphoma; metastasis, angiogenesis, and haematopoetic tissues; or inflammatory disorders such as asthma, allergic rhinitis, hypersensitivity lung diseases, hypersensitivity pneumonitis, eosinophilic pneumonias, delayed-type hypersensitivity, interstitial lung disease (ILD), idiopathic pulmonary fibrosis, ILD associated with rheumatoid arthritis, systemic lupus erythematosus, ankylosing sponylitis, systemic sclerosis, Sjogren's syndrome, systemic anaphylaxis or hypersensitivity responses, drug allergies, rheumatoid arthritis, psoriatic arthritis, multiple sclerosis, Alzheimer's disease, Parkinson's disease, atherosclerosis, myasthenia gravis, juvenile onset diabetes, glomerulonephritis, autoimmune throiditis, graft rejection, including allograft rejection or graft-versus-host disease, inflammatory bowel diseases and inflammatory dermatoses; or to treat eye diseases like glaucoma, diabethic retinopathy and age related macular degeneration; or to treat focal ischemic stroke, global cerebral ischemia, myocardial infarction, hind limb ischemia or peripheral ischemia; or to treat injury of the liver, kidney or lung; or to treat immunosuppression, including immunosuppression induced by chemotherapy, radiation therapy or graft/transplantation rejection, the β-hairpin peptidomimetics of the invention can be administered singly, as mixtures of several β-hairpin peptidomimetics, in combination with other anti-HIV agents, or antimicrobial agents or anti-cancer agents or anti-inflammatory agents, or in combination with other pharmaceutically active agents. The β-hairpin peptidomimetics of the invention can be administered per se or as pharmaceutical compositions.

Pharmaceutical compositions comprising β-hairpin peptidomimetics of the invention may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxilliaries which facilitate processing of the active β-hairpin peptidomimetics into preparations which can be used pharmaceutically. Proper formulation depends upon the method of administration chosen.

For topical administration the β-hairpin peptidomimetics of the invention may be formulated as solutions, gels, ointments, creams, suspensions, powders, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the β-hairpin peptidomimetics of the invention may be formulated in adequate solutions, preferably in physiologically compatible buffers such as Hink's solution, Ringer's solution, or physiological saline buffer. The solutions may contain formulatory agents such as suspending, stabilizing and/or dispersing agents. Alternatively, the β-hairpin peptidomimetics of the invention may be in powder form for combination with a suitable vehicle, e.g., sterile pyrogen-free water, before use.

For transmucosal administration, penetrants appropriate to the barrier to be permeated are used in the formulation as known in the art.

For oral administration, the compounds can be readily formulated by combining the active β-hairpin peptidomimetics of the invention with pharmaceutically acceptable carriers well known in the art. Such carriers enable the β-hairpin peptidomimetics of the invention to be formulated as tablets, pills, dragees, capsules, liquids, gels, syrups, slurries, suspensions, powders etc., for oral ingestion by a patient to be treated. For oral formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP); granulating agents; and binding agents. If desired, desintegrating agents may be added, such as cross-linked polyvinylpyrrolidones, agar, or alginic acid or a salt thereof, such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. In addition, flavoring agents, preservatives, coloring agents and the like may be added.

For buccal administration, the composition may take the form of tablets, lozenges, etc. formulated as usual.

The compounds may also be formulated in rectal or vaginal compositions such as suppositories together with appropriate suppository bases such as cocoa butter or other glycerides.

In addition to the formulations described above, the β-hairpin peptidomimetics of the invention may also be formulated as depot preparations. Such long acting formulations may be administered by implantation (e.g. subcutaneously or intramuscularly) or by intramuscular injection. For the manufacture of such depot preparations the β-hairpin peptidomimetics of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well known in the art. Certain organic solvents such as dimethylsulfoxide may also be employed. Additionally, the β-hairpin peptidomimetics of the invention may be delivered using a sustained-release system, such as semipermeable matrices of solid polymers containing the therapeutic agent (e.g. for coated stents). Various sustained-release materials have been established and are well known by those skilled in the art. Sustained-release capsules may, depending on their chemical nature, release the compounds for a few weeks up to over 100 days. Depending on the chemical nature and the biological stability of the therapeutic agent, additional strategies for protein stabilization may be employed.

As the β-hairpin peptidomimetics of the invention contain charged residues, they may be included in any of the above described formulations as such or as pharmaceutically acceptable salts. Pharmaceutically acceptable salts tend to be more soluble in aqueous and other protic solvents than are the corresponding free forms. Particularly suitable pharmaceutically acceptable salts include salts with carboxylic, phosphonic, sulfonic and sulfamic acids, e.g. acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalenedisulfonic acid, 2-, 3- or 4-methyl-benzenesulfonic acid, methylsulfuric acid, ethylsulfuric acid, dodecylsulfuric acid, N-cyclohexylsulfamic acid, N-methyl-, N-ethyl- or N-propyl-sulfamic acid, and other organic protonic acids, such as ascorbic acid. Suitable inorganic acids are for example hydrohalic acids, such as hydrochloric acid, sulfuric acid and phosphoric acid.

The β-hairpin peptidomimetics of the invention, or compositions thereof, will generally be used in an amount effective to achieve the intended purpose. It is to be understood that the amount used will depend on a particular application.

For topical administration to treat or prevent HIV infections a therapeutically effective dose can be determined using, for example, the in vitro assays provided in the examples. The treatment may be applied while the HIV infection is visible, or even when it is not visible. An ordinary skilled expert will be able to determine therapeutically effective amounts to treat topical HIV infections without undue experimentation.

For systemic administration, a therapeutically effective dose can be estimated initially from in vitro assays. For example, a dose can be formulated in animal models to achieve a circulating β-hairpin peptidomimetic concentration range that includes the $IC_{50}$ as determined in the cell culture. Such information can be used to more accurately determine useful doses in humans.

Initial dosages can also be determined from in vivo data, e.g. animal models, using techniques that are well known in the art. One having ordinary skill in the art could readily optimize administration to humans based on animal data.

Dosage amounts for applications as anti-HIV agents may be adjusted individually to provide plasma levels of the β-hairpin peptidomimetics of the invention which are sufficient to maintain the therapeutic effect. Therapeutically effective serum levels may be achieved by administering multiple doses each day.

In cases of local administration or selective uptake, the effective local concentration of the β-hairpin peptidomimetics of the invention may not be related to plasma concentration. One having the ordinary skill in the art will be able to optimize therapeutically effective local dosages without undue experimentation.

The amount of β-hairpin peptidomimetics administered will, of course, be dependent on the subject being treated, on the subject's weight, the severity of the affliction, the manner of administration and the judgement of the prescribing physician.

The anti-HIV therapy may be repeated intermittently while infections are detectable or even when they are not detectable. The therapy may be provided alone or in combination with other drugs, such as for example other anti-HIV agents or anti-cancer agents, or other antimicrobial agents.

Normally, a therapeutically effective dose of the β-hairpin peptidomimetics described herein will provide therapeutic benefit without causing substantial toxicity.

Toxicity of the β-hairpin peptidomimetics of the invention can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in humans. The dosage of the β-hairpin peptidomimetics of the invention lies preferably within a range of circulating concentrations that include the effective dose with little or no toxicity. The dosage may vary within the range depending upon the dosage form employed and the route of administration utilized. The exact formulation, route of administration and dose can be chosen by the individual physician in view of the patient's condition (see, e.g. Fingl et al. 1975, In: *The Pharmacological Basis of Therapeutics*, Ch. 1, p. 1).

The present invention may also include compounds, which are identical to the compounds of the general formula cyclo(-Tyr$^1$-His$^2$-Xaa$^3$-Cys$^4$-Ser$^5$-Ala$^6$-Aaa$^7$-Aaa$^8$-Arg$^9$-Tyr$^{10}$-Cys$^{11}$-Tyr$^{12}$-Xaa$^{13}$-Xaa$^{14}$-$^D$Pro$^{15}$-Pro$^{16}$-), disulfide bond between Cys$^4$ and Cys$^{11}$, except that one or more atoms are replaced by an atom having an atomic mass number or mass different from the atomic mass number or mass usually found in nature, e.g. compounds enriched in $^2$H (D), $^3$H, $^{11}$C, $^{14}$C, $^{129}$I etc. These isotopic analogs and their pharmaceutical salts and formulations are considered useful agents in the therapy and/or diagnostic, for example, but not limited to, where a fine-tuning of in vivo half-life time could lead to an optimized dosage regimen.

The following Examples illustrate the present invention but are not to be construed as limiting its scope in any way.

EXAMPLES

1. Peptide Synthesis

Coupling of the First Protected Amino Acid Residue to the Resin 1 g (1.4 mMol) 2-chlorotritylchloride resin (1.4 mMol/g; 100-200 mesh, copoly(styrene-1% DVB) polymer matrix; Barbs et al. *Tetrahedron Lett.* 1989, 30, 3943-3946) was filled into a dried flask. The resin was suspended in $CH_2Cl_2$ (5 mL) and allowed to swell at room temperature under constant shaking for 30 min. A solution of 0.98 mMol (0.7 eq) of the first suitably protected amino acid residue (see below) in $CH_2Cl_2$ (5 mL) mixed with 960 μl (4 eq) of diisopropylethylamine (DIEA) was added. After shaking the reaction mixture for 4 h at 25° C., the resin was filtered off and washed successively with $CH_2Cl_2$ (1×), DMF (1×) and $CH_2Cl_2$ (1×). A solution of $CH_2Cl_2$/MeOH/DIEA (17/2/1, 10 mL) was added to the resin and the suspension was shaken for 30 min. After filtration the resin was washed in the following order with $CH_2Cl_2$ (1×), DMF (1×), $CH_2Cl_2$ (1×), MeOH (1×), $CH_2Cl_2$ (1×), MeOH (1×), $CH_2Cl_2$ (2×), $Et_2O$ (2×) and dried under vacuum for 6 hours.

Loading was typically 0.6-0.7 mMol/g.

The following preloaded resins was prepared:

Fmoc-Pro-2-chlorotrityl resin.

The synthesis was carried out employing a Syro-peptide synthesizer (MultiSynTech) using 24-96 reaction vessels. In each vessel 0.04 mMol of the above resin was placed and the resin was swollen in $CH_2Cl_2$ and DMF for 15 min, respectively. The following reaction cycles were programmed and carried out:

| Step | Reagent | Time |
|---|---|---|
| 1 | DMF, wash | 2 × 1 min |
| 2 | 20% piperidine/DMF | 1 × 5 min, 1 × 15 min |
| 3 | DMF, wash | 5 × 1 min |
| 4 | 5 eq Fmoc amino acid/DMF +5 eq Py-BOP/DMF, 10 eq DIEA/DMF | 1 × 60 min |
| 5 | DMF, wash | 3 × 1 min |

Step 4 was repeated once.

Unless indicated otherwise, the final coupling of an amino acid was followed by Fmoc deprotection by applying steps 1-3 of the above described reaction cycle.

Amino Acid Building Block Syntheses
Synthesis of Fmoc-Orn(iPr,Boc)-OH

The synthesis of (2S)—$N^\alpha$-fluorenylmethoxylcarbonyl-$N^\omega,N^\omega$-tert-butyloxycarbonyl-isopropyl-2,5-diaminopentanoic acid was accomplished by suspending 15.2 g Fmoc-Orn-OH*HCl in 150 mL THF (0.26 M) followed by adding 375 mL acetone (132 eq) and 20.6 g sodium triacetoxyborohydride (2.5 eq). The reaction mixture was stirred for 2 h and subsequent to completion of the reaction (monitored by LC-MS) 120 mL of sat. $Na_2CO_3$-solution and 10.2 g $Boc_2O$ (1.2 eq) were added. After stirring overnight sat. $Na_2CO_3$-solution and $Boc_2O$ were added again twice in portions according to the remaining starting material. Following completion of the Boc-introduction hexane was added twice, separated, and the aqueous layer was acidified with 5 N $HCl_{aq}$ (pH=1) and extracted thrice with ethyl acetate thereafter. Finally, the combined organic layers were dried with $Na_2SO_4$ and evaporated to obtain the product as white foam. The amino acid building block Fmoc-Lys(iPr,Boc)-OH can be synthesized accordingly or is commercially available.

The amino acid building blocks Fmoc-Tyr(Me)-OH and Fmoc-$^D$Tyr(Me)-OH are commercially available as well.

Cyclization and Work Up of Backbone Cyclized Peptides
Cleavage of the Fully Protected Peptide Fragment After completion of the synthesis, the resin (0.04 mMol) was suspended in 1 mL (0.13 mMol, 3.4 eq) of 1% TFA in $CH_2Cl_2$ (v/v) for 3 minutes, filtered, and the filtrate was neutralized with 1 mL (0.58 mMol, 14.6 eq) of 10% DIEA in $CH_2Cl_2$ (v/v). This procedure was repeated three times to ensure completion of the cleavage. The filtrate was evaporated to dryness and a sample of the product was fully deprotected by using a cleavage mixture containing 95% trifluoroacetic acid (TFA), 2.5% water and 2.5% triisopropylsilane (TIS) to be analyzed by reverse phase-HPLC ($C_{18}$ column) and ESI-MS to monitor the efficiency of the linear peptide synthesis.

Cyclization of the Linear Peptide

The fully protected linear peptide (0.04 mMol) was dissolved in DMF (4 μMol/mL). Then 30.4 mg (0.08 mMol, 2 eq) of HATU, 10.9 mg (0.08 mMol, 2 eq) of HOAt and 28 μl (0.16 mMol, 4 eq) DIEA were added, and the mixture was vortexed at 25° C. for 16 hours and subsequently concentrated under high vacuum. The residue was partitioned between $CH_2Cl_2$ and $H_2O/CH_3CN$ (90/10: v/v). The $CH_2Cl_2$ phase was evaporated to yield the fully protected cyclic peptide.

Full Deprotection of the Cyclic Peptide

The cyclic peptide obtained was dissolved in 3 mL of the cleavage mixture containing 82.5% trifluoroacetic acid (TFA), 5% water, 5% thioanisole, 5% phenol and 2.5% ethanedithiole (EDT). The mixture was allowed to stand at 25° C. for 2.5 hours and thereafter concentrated under vacuum. After precipitation of the cyclic fully deprotected peptide in diethylether ($Et_2O$) at 0° C. the solid was washed twice with $Et_2O$ and dried.

Formation of Disulfide β-Strand Linkage and Purification

After full deprotection, the crude peptide was dissolved in 0.1 M ammonium acetate buffer (1 mg/1 mL, pH=7-8). DMSO (up to 5% by volume) was added and the solution was shaken overnight. Following evaporation the residue was purified by preparative reverse phase HPLC.

After lyophilisation the products were obtained as white powders and analysed by the following analytical method: Analytical HPLC retention times (RT, in minutes) were determined using a Ascentis Express C18 column, 50×3.0 mm, (cod. 53811-U-Supelco) with the following solvents A ($H_2O$+0.1% TFA) and B ($CH_3CN$+0.1% TFA) and the gradient: 0-0.05 min: 97% A, 3% B; 3.4 min: 33% A 67% B; 3.41-3.65 min: 3% A, 97% B; 3.66-3.7 min: 97% A, 3% B. Flow rate=1.3 mL/min; UV_Vis=220 nm.

Example 1

Starting resin was Fmoc-Pro-O-2-chlorotrityl resin, which was prepared as described above. To that resin $^D$Pro, finally at position 15, was grafted. The linear peptide was synthesized on solid support according to the procedure described above in the following sequence: Resin-Pro$^{16}$-$^D$Pro$^{15}$-Lys(iPr)$^{14}$-Gln$^{13}$-Tyr$^{12}$-Cys$^{11}$-Tyr$^{10}$-Arg$^9$-Orn(iPr)$^8$-$^D$Pro$^7$-Ala$^6$-Ser$^5$-Cys$^4$-Tyr$^3$-His$^2$-Tyr$^1$. Following a final Fmoc deprotection as described above, the peptide was cleaved from the resin, cyclized, deprotected and, after formation of the disulfide β-strand linkage as described above, purified as indicated above.

The HPLC-retention time (minutes) was determined using the analytical method as described above (UV-purity [after preparative HPLC]: 95%; RT: 1.56; [M+3H]/3=685.7).

Example 2

Starting resin was Fmoc-Pro-O-2-chlorotrityl resin, which was prepared as described above. To that resin $^D$Pro, finally at position 15, was grafted. The linear peptide was synthesized on solid support according to the procedure described above in the following sequence: Resin-Pro$^{16}$-$^D$Pro$^{15}$-Lys(iPr)$^{14}$-Gln$^{13}$-Tyr$^{12}$-Cys$^{11}$-Tyr$^{10}$-Arg$^9$-Orn(iPr)$^8$-$^D$Pro$^7$-Ala$^6$-Ser$^5$-Cys$^4$-Tyr(Me)$^3$-His$^2$-Tyr$^1$. Following a final Fmoc deprotection as described above, the peptide was cleaved from the resin, cyclized, deprotected and, after formation of the disulfide β-strand linkage as described above, purified as indicated above.

The HPLC-retention time (minutes) was determined using the analytical method as described above (UV-purity [after preparative HPLC]: 95%; RT: 1.7; [M+3H]/3=690.4).

Example 3

Starting resin was Fmoc-Pro-O-2-chlorotrityl resin, which was prepared as described above. To that resin $^D$Pro, finally at position 15, was grafted. The linear peptide was synthesized on solid support according to the procedure described above in the following sequence: Resin-Pro$^{16}$-$^D$Pro$^{15}$-Lys(iPr)$^{14}$-Gln$^{13}$-Tyr$^{12}$-Cys$^{11}$-Tyr$^{10}$-Arg$^9$-Dab$^8$-$^D$Tyr$^7$-Ala$^6$-Ser$^5$-Cys$^4$-Ala$^3$-His$^2$-Tyr$^1$. Following a final Fmoc deprotection as described above, the peptide was cleaved from the resin, cyclized, deprotected and, after formation of the disulfide β-strand linkage as described above, purified as indicated above.

The HPLC-retention time (minutes) was determined using the analytical method as described above (UV-purity [after preparative HPLC]: 95%; RT: 1.57; [M+3H]/3=658.3).

Example 4

Starting resin was Fmoc-Pro-O-2-chlorotrityl resin, which was prepared as described above. To that resin $^D$Pro, finally at position 15, was grafted. The linear peptide was synthesized on solid support according to the procedure described above in the following sequence: Resin-Pro$^{16}$-$^D$Pro$^{15}$-Lys(iPr)$^{14}$-Gln$^{13}$-Tyr$^{12}$-Cys$^{11}$-Tyr$^{10}$-Arg$^9$-Orn(iPr)$^8$-$^D$Tyr(Me)$^7$-Ala$^6$-Ser$^5$-Cys$^4$-Ala$^3$-His$^2$-Tyr$^1$. Following a final Fmoc deprotection as described above, the peptide was cleaved from the resin, cyclized, deprotected and, after formation of the disulfide β-strand linkage as described above, purified as indicated above.

The HPLC-retention time (minutes) was determined using the analytical method as described above (UV-purity [after preparative HPLC]: 95%; RT: 1.70; [M+3H]/3=681.7).

Example 5

Starting resin was Fmoc-Pro-O-2-chlorotrityl resin, which was prepared as described above. To that resin $^D$Pro, finally at position 15, was grafted. The linear peptide was synthesized on solid support according to the procedure described above in the following sequence: Resin-Pro$^{16}$-$^D$Pro$^{15}$-Lys(iPr)$^{14}$-Gln$^{13}$-Tyr$^{12}$-Cys$^{11}$-Tyr$^{10}$-Arg$^9$-Orn(iPr)$^8$-$^D$Tyr$^7$-Ala$^6$-Ser$^5$-Cys$^4$-Tyr$^3$-His$^2$-Tyr$^1$. Following a final Fmoc deprotection as described above, the peptide was cleaved from the resin, cyclized, deprotected and, after formation of the disulfide β-strand linkage as described above, purified as indicated above.

The HPLC-retention time (minutes) was determined using the analytical method as described above (UV-purity [after preparative HPLC]: 95%; RT: 1.60; [M+3H]/3=707.4).

Example 6

Starting resin was Fmoc-Pro-O-2-chlorotrityl resin, which was prepared as described above. To that resin $^D$Pro, finally at position 15, was grafted. The linear peptide was synthesized on solid support according to the procedure described above in the following sequence: Resin-Pro$^{16}$-$^D$Pro$^{15}$-Lys(iPr)$^{14}$-Gln$^{13}$-Tyr$^{12}$-Cys$^{11}$-Tyr$^{10}$-Arg$^9$-Orn(iPr)$^8$-$^D$Tyr(Me)$^7$-Ala$^6$-Ser$^5$-Cys$^4$-Tyr(Me)$^3$-His$^2$-Tyr$^1$. Following a final Fmoc deprotection as described above, the peptide was cleaved from the resin, cyclized, deprotected and, after formation of the disulfide β-strand linkage as described above, purified as indicated above.

The HPLC-retention time (minutes) was determined using the analytical method as described above (UV-purity [after preparative HPLC]: 95%; RT: 1.83; [M+3H]/3=717.0).

2. Biological Methods

2.1. Preparation of the Peptides

Lyophilized peptides were weighed on a Microbalance (Mettler MT5) and dissolved in DMSO to a final concentration of 10 mM. Stock solutions were kept at +4° C., light protected. The biological assays were carried out under assay conditions having less than 1% DMSO unlike indicated otherwise.

2.2. Cell Culture

Namalwa cells (CXCR4 natively expressing non-adherent cells, ATCC CRL-1432) were cultured in RPMI1640 plus 10% FBS, and pen/strept. HELA cells were maintained in RPMI1640 plus 10% FBS, pen/strept and 2 mM L-glutamine. Cos-7 cells were grown in DMEM medium with 4500 mg/mL glucose supplemented with 10% FCS, pen/strept and 2 mM L-glutamine. All cell lines were grown at 37° C. at 5% $CO_2$. Cell media, media supplements, PBS-buffer, HEPES, antibiotic/antimycotic, pen/strept, non essential amino acid, L-glutamine, β-mercaptoethanol and sera were purchased from Gibco (Pailsey, UK). All fine chemicals were supplied by Merck (Darmstadt, Germany).

2.3. Chemotactic Assay (Cell Migration Assay)

The chemotactic response of Namalwa cells (ATCC CRL-1432) to a gradient of stromal cell-derived factor 1α (SDF-1) was measured using a modified Boyden chamber chemotaxis system (ChemoTx; Neuroprobe). In this system, the upper chamber of each well is separated from the lower chamber containing the chemoattractant SDF-1 by a polycarbonate membrane (5 µm pore size). A circular area of that membrane in the region that covers each lower well is enclosed by a hydrophobic mask to retain the cell suspension within this area. The system was prepared by loading the bottom wells with aliquots of 30 µL of chemotaxis medium (RPMI 1640 without Phenol red+0.5% BSA) comprising either appropriate serial dilutions of peptides or no peptide at all in combination with SDF-1 (0.9 nM) or without the chemoattractant. The membrane was placed over the bottom wells, and aliquots of 50 µL of a suspension of Namalwa cells ($3.6 \times 10^6$ cells/mL) in chemotaxis medium, premixed with chemotaxis medium comprising either appropriate serial dilutions of peptides or no peptide at all, was delivered onto each of the hydrophobically limited regions of the upper surface of the membrane. The cells were allowed to migrate into the bottom chamber for 5 h at 37° C. in 5% $CO_2$. After this period, the membrane was removed and its topside was carefully wiped and washed with PBS to eliminate non-migrated cells. Migrated cells were transferred using a "funnel" adaptor to a receiving 96-well plate and the cell number was determined by using the CyQuant™ NF cell proliferation assay (Invitrogen) based on the measurement of cellular DNA content via fluorescent dye binding. Following the manufacturer's directions, 50 µL of CyQuant™ dye reagent/HBSS buffer (1/500 [v/v]) were added to each well of the above mentioned receiving 96-well plate. After incubation for 0.5 h at room temperature the plate was sealed and the fluorescence intensity of each sample was measured by using a Wallac 1420 VICTOR$^2$™ plate reader (PerkinElmer) with excitation at 485 nm and emission detection at 535 nm. Finally, the data were normalized by using the controls and $IC_{50}$-values were determined using GraphPad Prism™ (GraphPad) by fitting a logarithmic curve to the averaged datapoints.

2.4. Cytotoxicity Assay

The cytotoxicity of the peptides to HELA cells (Acc57) and COS-7 cells (CRL-1651) was determined using the MTT reduction assay (T. Mossman, *J. Immunol. Meth.* 1983, 65, 55-63; M. V. Berridge, A. S. Tan, *Arch. Biochem. Biophys.* 1993, 303, 474-482). Briefly, the method was as follows: 4000 HELA cells/well and 3400 COS-7 cells/well were seeded and grown in 96-well microtiter plates for 24 h at 37° C. at 5% $CO_2$. Thereafter, time zero (Tz) was determined by MTT reduction (see below). The supernatant of the remaining wells was discarded, and fresh medium and compounds in serial dilutions (12.5, 25 and 50 µM, triplicates; 0 µM, blank) were pipetted into the wells. After incubation of the cells for 48 h at 37° C. at 5% $CO_2$ the supernatant was discarded again and 100 µL MTT reagent (0.5 mg/mL in RPMI1640 and DMEM, respectively)/well was added. Following incubation at 37° C. for 2-4 h the media were aspirated and the cells were spiked (100 µL isopropanol/well). The absorbance of the solubilized formazan was measured at 595 nm ($OD_{595}$peptide). For each concentration averages were calculated from triplicates. The percentage of growth was calculated as follows: $(OD_{595}peptide - OD_{595}Tz)/(OD_{595}blank - OD_{595}Tz) \times 100\%$.

The $GI_{50}$ (Growth Inhibition) concentrations were calculated for each peptide by using a trend line function for the concentrations (50, 25, 12.5 and 0 µM), the corresponding percentages and the value 50, (=TREND ($C_{50}$:$C_0$,$\%_{50}$:$\%_0$, 50).

2.5. Hemolysis

The peptides were tested for their hemolytic activity against human red blood cells (hRBC). Fresh hRBC were washed four times with phosphate buffered saline (PBS) and centrifuged for 10 min at 3000×g. Compounds (100 µM) were incubated with 20% hRBC (v/v) for 1 h at 37° C. and shaking at 300 rpm. The final erythrocyte concentration was approximately $0.9 \times 10^9$ cells/mL. A value of 0% and 100% cell lysis, respectively, was determined by incubation of hRBC in the presence of PBS containing 0.001% acetic acid and 2.5% Triton X-100 in $H_2O$, respectively. The samples were centrifuged, the supernatants were 8-fold diluted in PBS buffer and the optical densities (OD) were measured at 540 nm. The 100% lyses value ($OD_{540}H_2O$) gave an $OD_{540}$ of approximately 0.5-1.0. Percent hemolysis was calculated as follows: ($OD_{540}$peptide/$OD_{540}H_2O$)×100%.

2.6. Plasma Stability

The stability of the peptides in human and mouse plasma was determined by applying the following method: 346.5 µL/deep well of freshly thawed human plasma (Basler Blutspende-dienst) and mouse plasma (Harlan Sera-Lab, UK), respectively, were spiked with 3.5 µL/well of compound dissolved in DMSO/$H_2O$ (90/10 [v/v], 1 mM, triplicate) and incubated at 37° C. At t=0, 15, 30, 60, 120, 240 and 1440 min aliquots of 50 µL were transferred to filtration plate wells containing 150 µL/well of 2% formic acid in acetonitrile. Following shaking for 2 min the occurred suspensions were filtrated by vacuum. 100 µL of each filtrate were transferred to a propylene microtiter plate and dried under $N_2$. The residual solids were reconstituted by adding 100 µL/well of water/acetonitrile, 95/5 (v/v)+0.2% formic acid and analyzed by LC/MS as follows: Column: Waters, XBridge C18, mobile phases: (A) water+0.1% formic acid and (B) acetonitrile/water, 95/5 (v/v)+0.1% formic acid, gradient: 5%-100% (B) in 1.8 minutes, electrospray ionization, MRM detection (triple quadrupole). The peak areas were determined and triplicate values are averaged. The stability is expressed in percent of the initial value at t=0·(tx/t0×100). By using the TREND function of EXCEL (Microsoft Office 2003) $T_{1/2}$ were determined.

2.7. Plasma Protein Binding

495 µL aliquots of human plasma (Basler Blutspendedienst) as well as 495 µL aliquots of PBS were placed in individual deepwells of a polypropylene plate (Greiner) and spiked each with 5 µL of 1 mM solutions of peptides in 90% DMSO. After shaking the plate for 2 min at 600 rpm 150 µL aliquots of the plasma/peptide mixtures were transferred in triplicates to the polypropylene filter plate (10 kDa, Millipore) whereas 150 µL aliquots of the PBS/peptide mixtures were transferred either to the individual wells of the filter plate (filtered controls) or directly into the individual wells of the receiving plate (Greiner) (non-filtered controls). The plate sandwich consisting of filter and receiving plate was incubated for 1 h at 37° C. and subsequently centrifuged at 3220 g for 2 h at 15° C. The filtrates in the receiving plate were analysed by LC/MS as follows: Column: Waters, XBridge C18, mobile phases: (A) water+0.1% formic acid and (B) acetonitrile/water, 95/5 (v/v)+0.1% formic acid, gradient: 5%-100% (B) in 1.8 min, electrospray ionization, MRM detection (triple quadrupole). The peak areas were determined and triplicate values are averaged. The binding is expressed in percent of the filtered and non-filtered controls by 100−(100×$T_{1h}$/$T_{ctr}$). Finally the average of these values is calculated.

The results of the experiments described under 2.3-2.7 are indicated in the Tables 1, 2, 3 and 4 herein below.

2.8. Pharmacokinetic Study (PK)

For the compounds of Ex. 1, Ex. 2, Ex. 3, Ex. 4, Ex. 5 and Ex. 6 pharmacokinetic studies after intravenous (i.v.) administration were performed.

30 grams (±20%) male CD-1 mice obtained from Charles River Laboratories Deutschland GmbH were used. The vehicle, phosphate buffered saline, was added to give a final concentration of 0.5 mg/mL of the compound. The volume was 2 mL/kg and the compound was injected to give a final intravenous dose of 1 mg/kg. Approximately 300-400 µL of blood was removed under light isoflurane anesthesia by cardiac puncture at predetermined time intervals (5, 15, 30 min and 1, 2, 3, 4, hours) and added to heparinized tubes. Plasma was removed from pelleted cells upon centrifugation and frozen at −80° C. prior to HPLC-MS analysis.

Preparation of Plasma Calibration- and Plasma Study-Samples

Aliquots of 50 µL each of mouse plasma of untreated aminals ("blank" mouse plasma) were spiked with known amounts of the compounds Ex. 1, Ex. 2, Ex. 3, Ex. 4, Ex. 5 and Ex. 6 in order to obtain 10 plasma calibration samples for each compound in the range 1-4000 ng/mL. Aliquots of 50 µL each of mouse plasma from treated animals were used as plasma study samples.

Extraction of Plasma Calibration- and Plasma Study-Samples

All plasma samples were spiked with an appropriate internal standard and extracted with acetonitrile containing 2% formic acid. Supernatants were evaporated to dryness under nitrogen and the remaining solids reconstituted in water/acetonitrile 95/5 (v/v)+0.2% formic acid.

LC-MS/MS-Analysis

Extracts were then analyzed by reverse-phase chromatography (Acquity BEH C18, 100×2.1 mm, 1.7 µm column, Waters for Ex. 1 and Acquity HSS C18 SB, 100×2.1 mm, 1.8 µm column, Waters for Ex. 2, Ex. 3, Ex. 4, Ex. 5 and Ex. 6), using the following conditions: Ex. 1, mobile phases: (A) water/acetonitrile 95/5 (v/v)+0.1% formic acid, (B) acetonitrile/water 95/5 (v/v)+0.1% formic acid, gradient: 1% (B) 0-0.1 min, 15% (B) 0.1-2.5 min for Ex. 1 and 1% (B) 0-0.1 min, 40% (B) 0.1-2.5 min for Ex. 2, Ex. 3, Ex. 4, Ex. 5 and Ex. 6. The detection and quantification was performed by mass spectrometry, with electrospray interface in positive mode and selective fragmentation of analytes (4000 Q Trap mass spectrometer, AB Sciex).

Pharmacokinetic Evaluation

PK parameters were calculated by WinNonLin™ software version 5.3 (Pharsight-A Certara™ Company, Mountain View, Calif. 94041 USA) using a one-compartmental model analysis. PK parameters were determined by least-square fitting of the model to the experimental data.

The results of the experiments described in 2.8 are indicated in Tables 5a and 5b herein below.

2.9. Drug Loading Calculations Via Maintainance Dose Rate (Rate of Infusion)

The drug load for an implant comprising a peptide of the invention was calculated following the basic principles in pharmacokinetics (see also J. Gabrielsson, D. Weiner, "Pharmacokinetics and Pharmaco-dynamics Data Analysis: Concepts and Applications", 4$^{th}$ edition, Swedish Pharmaceutical Press, Stockholm, Sweden, 2006) whereby the maintainance dose rate (rate of infusion, $R_{in}$) can be defined as the rate at which a drug is to be administered to reach a steady state of a certain dose in the plasma. The maintainance dose rate can be expressed using the correlation $R_{in}$

[g/(h*kg)]=$CL_{iv}$ [L/(h*kg)]×$C_{ss,eff}$[g/L], wherein $CL_{iv}$ is the clearance (i.v.—admin.) and $C_{ss,eff}$ the effective concentration of the drug in the plasma at steady state considering an efficacy margin A: $C_{ss,eff}$ [g/L]=A×($IC_{50}/f_u$)×MW [(mol/L)*(g/mol)]. Therefore, the total amount of a drug loaded into an implant providing for a constant effective concentration of that drug in the plasma for a certain period of time in a subject of a certain body weight can be calculated by applying the following correlation:

Drug$_{load}$ [g/subject]=$R_{in}$ [g/(h*kg)]×duration [h]×BW [kg/subject].

The results of the calculations described in 2.9 are indicated in Table 6 herein below and based on the data given in Tables 1, 4 and 5b. Further pre-conditions are an efficacy margin of A=3, a study duration of 672 h (28 days) and a body weight of a human subject of 70 kg. The glomerular filtration rate (GFR) which mainly influences the clearance of the peptides is highly dependent on the species. In general, the GFR of humans is averaged to be 107 mL/(h*kg) compared to the GFR of mouse being 840 mL/(h*kg). Therefore, the $CL_{iv}$-mouse values indicated in Table 5b were allometrically scaled by 107 mL/(h*kg)/840 mL/(h*kg)=0.127 before employed in the above described correlations.

3.0. HSC Mobilization in Mouse

For the compounds of Ex. 1 and Ex. 2 a HSC mobilization study was performed consisting of a time-response study to assess the time of maximum mobilization after dosing and a subsequent dose-response study.

Time-Response Study

Male C57Bl/6 mice (Janvier, France; n=5 for Ex. 1, n=3 for Ex. 2) received bolus i.p. injections of Ex. 1 and Ex. 2, respectively, (5 mg/kg) dissolved in 10 μL of water per g mouse weight containing 0.9% NaCl. Blood was withdrawn from the cheek pouch into EDTA coated tubes for the time points 0, 0.5, 1, 2, 4, 6 and 8 hrs after administration. The colony forming unit in culture counts (CFU-C counts) were determined by performing a CFU-C assay as described below. The results of the time-response study for Ex. 1 and Ex. 2 are indicated in Tables 7a and 7b.

Dose-Response Study

Male C57Bl/6 mice (Janvier, France; n=5 per dose group for Ex. 1, n=3 per dose group for Ex. 2) received bolus i.p. injections of Ex. 1 and Ex. 2, respectively, at doses of 0.5, 1.5, 5 and 15 mg/kg (compound dissolved in 10 μL of water per g mouse weight containing 0.9% NaCl). Blood was collected as described above at the time of maximum mobilization for Ex. 1 (4 h) and Ex. 2 (2 h), respectively. The results of the dose-response study for Ex. 1 and Ex. 2 are indicated in Tables 8a and 8b.

CFU-C Assay

CFU-C counts were determined by culturing aliquots of lysed peripheral blood in standard semi-solid progenitor cell culture medium. In brief, a defined amount of blood was washed with PBS buffer (Gibco®) containing 0.5% bovine serum albumin, followed by red blood cell lysis in hypotonic $NH_4Cl$ buffer (Sigma) and a second wash step. The cell pellet was resuspended in DMEM (Gibco®) containing 10% FCS, suspended in 2 mL of commercially available, cytokine-replete methylcellulose medium for murine cells (Cell Systems, USA), and plated in duplicate into 35 mm cell culture dishes. CFU-C were scored after 7-8 days incubation under standard conditions (20% $O_2$, saturated humidity, 5% $CO_2$, 37° C.). Peripheral blood cellularity was analyzed using an automated blood count machine (Drew Scientific).

$Log_{10}$ Dose-Response Curve and $ED_{50}$

Figure 1:
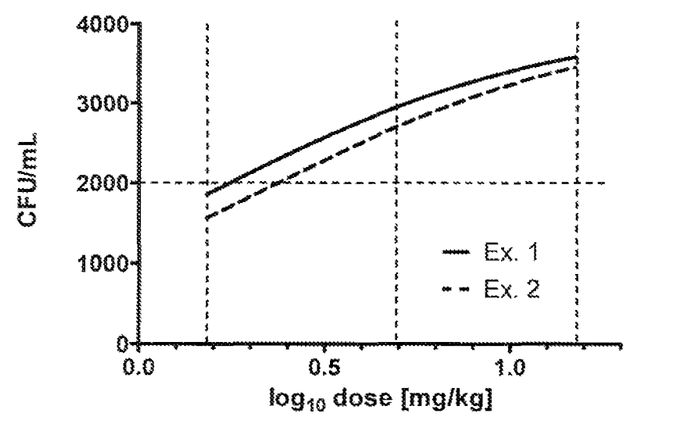
FIG. 1 is a log 10 dose-response curves of Ex. 1 and Ex. 2 based on the CFU/mL-values for the doses 1.5, 5 and 15 mg/kg as indicated in Tables 8a and 8b, respectively, which was fitted using the sigmoidal dose-response fitting function in GraphPad Prism, version 5.03.

The $log_{10}$ dose-response curves of Ex. 1 and Ex. 2 based on the CFU/mL-values for the doses 1.5, 5 and 15 mg/kg as indicated in Tables 8a and 8b, respectively, are shown in FIG. 1 and fitted using the sigmoidal dose-response fitting function in Graph Pad Prism, version 5.03. Considering the curve progressions of both compounds the dose-responses are constrained to a maximum response of 4000 CFU/mL. The $ED_{50}$-values indicated in Table 9 are therefore corresponding to a response of 2000 CFU/mL.

TABLE 1

| Ex. | $IC_{50}$ [nM] ± SD, CXCR4 receptor |
|---|---|
| 1 | 0.42 ± 0.1 |
| 2 | 0.69 ± 0.43 |
| 3 | 0.11 ± 0.01 |
| 4 | 0.18 ± 0.09 |
| 5 | 0.43 ± 0.24 |
| 6 | 0.09 ± 0.09 |

TABLE 2

| | Cytotoxicity | | Hemolysis at |
|---|---|---|---|
| Ex. | Hela Cells $GI_{50}$ [μM] | Cos-7 Cells $GI_{50}$ [μM] | 100 μM [%] |
| 1 | >50 | >50 | 1.0 |
| 2 | >41 | >50 | 1.0 |
| 3 | >50 | >50 | 1.0 |
| 4 | >50 | >50 | 0 |
| 5 | >50 | >50 | 3.5 |
| 6 | >50 | >50 | 2 |

TABLE 3

| | Plasma stability | | | |
|---|---|---|---|---|
| Ex. | human pl. $T_{1/2}$ [min] | human pl. cpd left at 1440 min [%] | mouse pl. $T_{1/2}$ [min] | mouse pl. cpd left at 1440 min [%] |
| 1 | 1440 | 77 | 1440 | 100 |
| 2 | 1440 | 100 | 1440 | 100 |
| 3 | 1440 | 100 | 1440 | 98 |
| 4 | 1440 | 94 | 1440 | 60 |
| 5 | 1440 | 92 | 1440 | 81 |
| 6 | 1440 | 83 | 1440 | 68 |

TABLE 4

| Ex. | Plasma protein binding [%] | Fraction unbound, $f_u$ |
|---|---|---|
| 1 | 30 | 0.7 |
| 2 | 48 | 0.52 |
| 3 | 48 | 0.52 |
| 4 | 56 | 0.44 |
| 5 | 54 | 0.46 |
| 6 | 63 | 0.37 |

TABLE 5a

| Time [h] | Calc. Conc. [ng/mL] | Num. of anim. pool. | Calc. Conc. [ng/mL] | Num. of anim. pool. | Calc. Conc. [ng/mL] | Num. of anim. pool. |
|---|---|---|---|---|---|---|
| | Ex. 1 i.v. route Dose: 1 mg/kg | | Ex. 2 i.v. route Dose: 1 mg/kg | | Ex. 3 i.v. route Dose: 1 mg/kg | |
| 0.083 | 1723 | 3 | 1430 | 2 | 1168 | 3 |
| 0.25 | 989 | 3 | 1297 | 3 | 999 | 3 |
| 0.5 | 947 | 3 | 836 | 3 | 442 | 3 |
| 1 | 373 | 3 | 578 | 3 | 402 | 3 |
| 2 | 129 | 3 | 234 | 3 | 136 | 3 |
| 3 | 15 | 3 | 68 | 3 | 26 | 3 |
| 4 | 7 | 3 | 22 | 3 | 12 | 3 |
| | Ex. 4 i.v. route Dose: 1 mg/kg | | Ex. 5 i.v. route Dose: 1 mg/kg | | Ex. 6 i.v. route Dose: 1 mg/kg | |
| 0.083 | 1615 | 3 | 1313 | 2 | 686 | 3 |
| 0.25 | 869 | 3 | 984 | 3 | 435 | 3 |
| 0.5 | 775 | 3 | 350 | 3 | 215 | 3 |
| 1 | 504 | 3 | 503 | 3 | 75 | 3 |
| 2 | 159 | 3 | 150 | 3 | 36 | 3 |
| 3 | 25 | 3 | 49 | 3 | 13 | 3 |
| 4 | 13 | 3 | 33 | 3 | 7 | 3 |

TABLE 5b

| i.v. route | Ex. 1 | Ex. 2 | Ex. 3 | Ex. 4 | Ex. 5 | Ex. 6 |
|---|---|---|---|---|---|---|
| Dose [mg/kg] | 1 | 1 | 1 | 1 | 1 | 1 |
| $V_{dis}$ [mL/kg] | 547 | 635 | 762 | 607 | 1039 | 2975 |
| CL [mL/h/kg] | 868 | 659 | 1113 | 744 | 836 | 2446 |
| $AUC_{0-\infty}$ [ng * h/mL] | 1151 | 1518 | 898 | 1345 | 1196 | 409 |
| $C_{max}$ [ng/mL] | 1829 | 1575 | 1313 | 1615 | 1313 | 686 |
| Half-life [h] | 0.4 | 0.7 | 0.5 | 0.6 | 0.9 | 0.8 |

TABLE 6

| Ex. | Molecular Weight (salt free), MW [g/Mol] | $CL_{iv}$, human (allometric scaled) [mL/h/kg] | $Drug_{load}$ [mg] ± SD |
|---|---|---|---|
| 1 | 2054.40 | 110 | 19.2 ± 4.6 |
| 2 | 2068.42 | 84 | 32.7 ± 20.4 |
| 3 | 1972.25 | 141 | 8.3 ± 0.7 |
| 4 | 2042.38 | 94 | 11.1 ± 5.5 |
| 5 | 2120.45 | 106 | 29.7 ± 16.6 |
| 6 | 2148.51 | 311 | 22.9 ± 22.9 |

TABLE 7a

| Ex. 1 | Baseline | 0.5 h | 1 h | 2 h | 4 h | 6 h | 8 h |
|---|---|---|---|---|---|---|---|
| CFU/mL ± SD | 129 ± 12 | 511 ± 85 | 2208 ± 262 | 2592 ± 450 | 3109 ± 537 | 1857 ± 281 | 588 ± 161 |

TABLE 7b

| Ex. 2 | Baseline | 0.5 h | 1 h | 2 h | 4 h | 6 h | 8 h |
|---|---|---|---|---|---|---|---|
| CFU/mL ± SD | 242 ± 26 | 839 ± 48 | 1020 ± 262 | 2894 ± 329 | 1929 ± 643 | 1164 ± 151 | 373 ± 96 |

TABLE 8a

| Ex. 1 | 0 [mg/kg] | 0.5 [mg/kg] | 1.5 [mg/kg] | 5 [mg/kg] | 15 [mg/kg] |
|---|---|---|---|---|---|
| CFU/mL ± SD | 129 ± 12 | 974 ± 57 | 1672 ± 233 | 3325 ± 310 | 3289 ± 431 |

TABLE 8b

| Ex. 2 | 0 [mg/kg] | 0.5 [mg/kg] | 1.5 [mg/kg] | 5 [mg/kg] | 15 [mg/kg] |
|---|---|---|---|---|---|
| CFU/mL ± SD | 242 ± 26 | n.d. | 1314 ± 463 | 2894 ± 329 | 3589 ± 576 |

TABLE 9

| | $ED_{50}$ [mg/kg] | Confidence interval 95% |
|---|---|---|
| Ex. 1 | 1.76 | 0.57-5.39 |
| Ex. 2 | 2.38 | 1.15-4.89 |

The invention claimed is:

1. A method for treating HIV infections in a healthy individual, comprising:

administering a compound of formula (I), in free form or in a pharmaceutically acceptable salt form, to a healthy individual cyclo(-Tyr$^1$-His$^2$-Xaa$^3$-Cys$^4$-Ser$^5$-Ala$^6$-Xaa$^7$-Xaa$^8$-Arg$^9$-Tyr$^{10}$-Cys$^{11}$-Tyr$^{12}$-Xaa$^{13}$-Xaa$^{14}$-$^D$Pro$^{15}$-Pro$^{16}$-)  (I), in which Xaa$^3$ is Ala; Tyr; or Tyr(Me), Tyr(Me) is (2S)-2-amino-(4-methoxyphenyl)-3-propionic acid, Xaa$^7$ is $^D$Tyr; $^D$Tyr(Me); or $^D$Pro, $^D$Tyr(Me) is (2R)-2-amino-(4-methoxyphenyl)-3-propionic acid, or, Xaa$^8$ is Dab; or Orn(iPr), Dab is (2S)-2,4-diaminobutyric acid, Orn(iPr) is (2S)—N$^\omega$-isopropyl-2,5-diaminopentanoic acid, Xaa$^{13}$ is Gln; or Glu,

Xaa$^{14}$ is Lys(iPr),

Lys(iPr) is (2S)—N$^\omega$-isopropyl-2,6-diaminohexanoic acid, all of the amino acid residues, which are not explicitly designated as D-amino acid residues, are L-amino acid residues, and the two —SH groups in the two L-cysteine residues Cys⁴ and Cys¹¹ are replaced by one —S—S— group.

2. A method for treating HIV infections in an HIV infected patient, comprising:
administering a compound of formula (I), in free form or in a pharmaceutically acceptable salt form, to an HIV infected patient (I), in which
Xaa³ is Ala; Tyr; or Tyr(Me),
Tyr(Me) is (2S)-2-amino-(4-methoxyphenyl)-3-propionic acid,
Xaa⁷ is ᴰTyr; ᴰTyr(Me); or ᴰPro,
ᴰTyr(Me) is (2R)-2-amino-(4-methoxyphenyl)-3-propionic acid, or,
Xaa⁸ is Dab; or Orn(iPr),
Dab is (2S)-2,4-diaminobutyric acid,
Orn(iPr) is (2S)—Nᵂ-isopropyl-2,5-diaminopentanoic acid,
Xaa¹³ is Gln; or Glu,
Xaa¹⁴ is Lys(iPr),
Lys(iPr) is (2S)—Nᵂ-isopropyl-2,6-diaminohexanoic acid,
all of the amino acid residues, which are not explicitly designated as D-amino acid residues, are L-amino acid residues, and
the two —SH groups in the two L-cysteine residues Cys⁴ and Cys¹¹ are replaced by one —S—S— group.

3. The method according to claim 1, wherein the compound of the formula I is administered with at least one selected from the group consisting of a carrier, a diluent and an excipient.

4. The method according to claim 2, wherein the compound of the formula I is administered with at least one selected from the group consisting of a carrier, a diluent and an excipient.

5. The method according to claim 3, wherein the at least one carrier, excipient and diluent is selected from the group consisting of sugar, cellulose preparations, water, glycols, oils and alcohols.

6. The method according to claim 4, wherein the at least one carrier, excipient and diluent is selected from the group consisting of sugar, cellulose preparations, water, glycols, oils and alcohols.

7. The method according to claim 5, wherein the sugar is selected from the group consisting of lactose, sucrose, mannitol and sorbitol.

8. The method according to claim 6, wherein the wherein the sugar is selected from the group consisting of lactose, sucrose, mannitol and sorbitol.

9. The method according to claim 5, wherein the cellulose preparation is selected from the group consisting of maize starch, wheat starch, rice starch, potato starch, gelatin, gum tragacanth, methyl cellulose, hydroxypropylmethyl cellulose, sodium carboxymethylcellulose, and polyvinylpyrrolidone (PVP).

10. The method according to claim 6, wherein the cellulose preparation is selected from the group consisting of maize starch, wheat starch, rice starch, potato starch, gelatin, gum tragacanth, methyl cellulose, hydroxypropylmethyl cellulose, sodium carboxymethylcellulose, and polyvinylpyrrolidone (PVP).

11. A method for manufacturing a medicament for treating HIV infections, comprising:
formulating a pharmaceutical composition with a compound of formula (1), in free form or in a pharmaceutically acceptable salt form, with one or more physiologically acceptable carriers, diluents, excipients or auxiliaries (I), in which
Xaa³ is Ala; Tyr; or Tyr(Me),
Tyr(Me) is (2S)-2-amino-(4-methoxyphenyl)-3-propionic acid,
Xaa⁷ is ᴰTyr; ᴰTyr(Me); or ᴰPro,
ᴰTyr(Me) is (2R)-2-amino-(4-methoxyphenyl)-3-propionic acid, or,
Xaa⁸ is Dab; or Orn(iPr),
Dab is (2S)-2,4-diaminobutyric acid,
Orn(iPr) is (2S)—Nᵂ-isopropyl-2,5-diaminopentanoic acid,
Xaa¹³ is Gln; or Glu,
Xaa¹⁴ is Lys(iPr),
Lys(iPr) is (2S)—Nᵂ-isopropyl-2,6-diaminohexanoic acid,
all of the amino acid residues, which are not explicitly designated as D-amino acid residues, are L-amino acid residues, and
the two —SH groups in the two L-cysteine residues Cys⁴ and Cys¹¹ are replaced by one —S—S— group.

* * * * *